(12) United States Patent
Derrieu et al.

(10) Patent No.: US 10,143,701 B2
(45) Date of Patent: *Dec. 4, 2018

(54) COMPOSITIONS FOR ORAL ADMINISTRATION TO ANIMALS, PRODUCTION METHODS THEREOF AND USES OF SAME

(71) Applicant: Friulchem Spa, Vivaro (IT)

(72) Inventors: Guy Derrieu, Cagnes-sur-Mer (FR); Giancarlo Mazzola, Bedano (CH)

(73) Assignee: FRIULCHEM SPA, Vivaro (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/424,774

(22) PCT Filed: Aug. 29, 2013

(86) PCT No.: PCT/EP2013/067934
§ 371 (c)(1),
(2) Date: Feb. 27, 2015

(87) PCT Pub. No.: WO2014/033230
PCT Pub. Date: Mar. 6, 2014

(65) Prior Publication Data
US 2015/0216887 A1 Aug. 6, 2015

(30) Foreign Application Priority Data

Aug. 31, 2012 (WO) .......................... EP2012/067005

(51) Int. Cl.

| | | |
|---|---|---|
| A23P 30/00 | (2016.01) | |
| A61K 31/7048 | (2006.01) | |
| A23K 40/25 | (2016.01) | |
| A23K 20/184 | (2016.01) | |
| A23K 20/168 | (2016.01) | |
| A61K 9/00 | (2006.01) | |
| A61K 31/722 | (2006.01) | |
| A61K 31/737 | (2006.01) | |
| A61K 31/4985 | (2006.01) | |
| A61K 31/506 | (2006.01) | |
| A61K 31/365 | (2006.01) | |
| A61K 31/505 | (2006.01) | |
| A61K 47/02 | (2006.01) | |
| A61K 47/10 | (2017.01) | |
| A61K 47/12 | (2006.01) | |
| A61K 47/14 | (2017.01) | |
| A61K 47/26 | (2006.01) | |
| A61K 47/42 | (2017.01) | |
| A61K 47/44 | (2017.01) | |
| A61K 47/46 | (2006.01) | |
| A23K 40/20 | (2016.01) | |
| A23K 10/20 | (2016.01) | |
| A23K 10/30 | (2016.01) | |
| A23K 20/174 | (2016.01) | |
| A23K 20/158 | (2016.01) | |
| A23K 20/163 | (2016.01) | |

(Continued)

(52) U.S. Cl.
CPC .......... *A61K 31/7048* (2013.01); *A23K 10/20* (2016.05); *A23K 10/30* (2016.05); *A23K 20/10* (2016.05); *A23K 20/158* (2016.05); *A23K 20/163* (2016.05); *A23K 20/168* (2016.05); *A23K 20/174* (2016.05); *A23K 20/184* (2016.05); *A23K 20/195* (2016.05); *A23K 20/30* (2016.05); *A23K 40/20* (2016.05); *A23K 40/25* (2016.05); *A23K 50/20* (2016.05); *A23K 50/40* (2016.05); *A23P 30/00* (2016.08); *A61K 9/0056* (2013.01); *A61K 31/365* (2013.01); *A61K 31/4985* (2013.01); *A61K 31/505* (2013.01); *A61K 31/506* (2013.01); *A61K 31/722* (2013.01); *A61K 31/737* (2013.01); *A61K 47/02* (2013.01); *A61K 47/10* (2013.01); *A61K 47/12* (2013.01); *A61K 47/14* (2013.01); *A61K 47/26* (2013.01); *A61K 47/42* (2013.01); *A61K 47/44* (2013.01); *A61K 47/46* (2013.01)

(58) Field of Classification Search
CPC ....... A23P 30/00; A23K 50/40; A23K 20/158; A61K 47/26; A61K 9/0056
USPC .................. 514/30, 250; 264/330
See application file for complete search history.

(56) References Cited

U.S. PATENT DOCUMENTS 6,340,471 B1 * 1/2002 Kershman ............ A61K 9/0056
424/439
6,455,083 B1 * 9/2002 Wang .................. A01K 15/026
426/104

(Continued)

OTHER PUBLICATIONS

Vetstreet, titled Antibiotic Therapy for Ear Infections, published Dec. 29, 2011.*

(Continued)

Primary Examiner — Yanzhi Zhang
(74) Attorney, Agent, or Firm — Banner & Witcoff, Ltd.

(57) ABSTRACT

The invention relates to a method for the production of a time-stable, solid appetizing composition and to the use thereof, said composition comprising at least one active substance which is introduced in the final production step, by adding same to the already formed mixture of other components at ambient temperature, without the use of water or heat. The composition is intended for use as a drug, a nutraceutical or a food supplement for oral administration to mammals, except humans, in particular for pets such as dogs, cats or horses. The stable solid composition is obtained by compressing the mixture using a press for compressing formulations having a high fat content.

22 Claims, 2 Drawing Sheets

(51) Int. Cl.
*A23K 20/10* (2016.01)
*A23K 20/195* (2016.01)
*A23K 20/20* (2016.01)
*A23K 50/20* (2016.01)
*A23K 50/40* (2016.01)

(56) References Cited

U.S. PATENT DOCUMENTS 7,431,941 B2 * 10/2008 Besins ................ A61K 9/4858
424/456
2007/0128251 A1 * 6/2007 Paulsen ................ A61K 9/0056
424/439

OTHER PUBLICATIONS

Armin H. Gerhardt; title: Fundamentals of Tablet Compression; Journal of GXP Compliance; vol. 14, No. 1, pp. 70-79; Winter 2010.*

* cited by examiner

COMPOSITIONS FOR ORAL ADMINISTRATION TO ANIMALS, PRODUCTION METHODS THEREOF AND USES OF SAME

RELATED APPLICATION DATA

This application is a National Stage Application under 35 U.S.C. 371 of co-pending PCT application number PCT/EP2013/067934 designating the United States and filed Aug. 29, 2013; which claims the benefit of PCT application number PCT/EP2012/067005 and filed Aug. 31, 2012 each of which are hereby incorporated by reference in their entireties.

The present invention relates to the field concerning the preparing of palatable compositions for therapeutic purposes, more particularly to improve oral administration and to guarantee treatment compliance, that are formulated in solid form for animals (domestic, bred or wild).

At the current time developments are being seen in the care given to animals, and the oral route is becoming a priority route for administering medications by health professionals or owners, this being particularly true for nutraceutical products. The usual route for parenteral administration of medications in particular (intramuscular, sub-cutaneous, intradermal or intravenous), have a number of drawbacks. For example the intramuscular or sub-cutaneous routes may be the cause of haematomas or abscesses. The intravenous route often requires the services of a specialist (veterinary surgeon). As for the intradermal route this requires the use of solvents to allow the active molecules to pass through the skin barrier. These parenteral routes of administration also require the restraining of animals. In addition, some active substances are difficult to formulate in parenteral dosage forms. Finally, some active substances only exert their therapeutic action in animals if they can arrive directly in the digestive tract. For compositions to be accepted by an animal, they must be palatable so that they can be absorbed, after which animal satisfaction will be seen as the demanding for more. It is this satisfaction that is sought after and will be highly appreciated by animal owners.

It is known that the natural acceptance and consumption of a composition by an animal is based on two main characteristics of the dosage form: palatability and texture of the composition, and to a lesser extent the shape and size thereof.

Two other parameters must be added thereto:
  full control over the quantity of one or more active substances, whether the composition is a medication, nutraceutical or food supplement, and
  the cost of the composition, in particular if it is a nutraceutical or food supplement.

The dose formulations adapted for administering compositions via oral route or per os are generally in liquid form (e.g. syrups, solutions or drinkable suspensions, drops . . . ), in semisolid form (e.g. pastes for oral administration) or solid form. The solid forms frequently used per os for the animal population are in various formulations of different type and obtained using different methods. For example a distinction is made between tablets, pills, hard capsules, soft capsules, chewable gums, pellets . . . . It has chiefly been ascertained, for heed of treatment via oral route (i.e. heed of directions and recommendations given by the health professional for the taking of medication) that treatment is not always properly followed on account of the difficulty in administering treatments in full to animals. The administering of medications to animals in solid dosage form via oral route is often difficult on account of the bad taste of some active substances or some excipients contained in the medication and the much developed sense of smell and taste in animals. It has been observed in animals that the main reason which makes it difficult even impossible to properly follow oral treatment is the lack of palatability of the medication. The same applies to nutraceuticals or food supplements. Animal owners are particularly sensitive to the reactions of their animals when a composition needs to be taken. A composition given to an animal should be a source of pleasure shared by both owner and animal.

Appetency is defined as the psychological state corresponding to a desire to absorb a food or drink in response to the perceiving of the organoleptic characteristics of this product. The capacity to arouse appetency is called palatability. The combination of these characteristics determines the appeal of a product to be taken by oral route by animals that are fed normally. More particularly, the palatability of a medication plays a large part in the refusal or acceptance by an animal for spontaneous taking of treatment and for repeated taking thereof over sometimes long periods. Some treatments may have to be taken daily and even over a lifetime.

The palatability of a medication, a nutraceutical or food supplement administered via oral route leads to the acceptance and voluntary ingestion thereof by an animal. This palatability can be measured by a general appetency test taking into account different parameters of the composition formulated in solid form, such as the spontaneous taking thereof from the hand or on the ground, or the consumption thereof even if it is given over several times or taken at regular intervals by the animal.

Texture is defined as a physical state corresponding to a formulation arranged in a certain manner by production technology. It is on texture that hardness, brittleness, softness, elasticity, colour of the composition all depend.

Regarding the parameters of shape or size, these facilitate taking hold of the composition or the absorption thereof at a single time.

In the prior art, numerous solutions, whether or not combining these two major parameters even the other parameters, have been proposed to facilitate the absorption of medication in particular by an animal.

Concerning appetency, several methods have been proposed:

One first option is to mask the unpleasant taste and/or smell of the constituent(s), chiefly one or more active substances, by the encapsulation or coating thereof.

The following patent applications: EP 0 997 143, EP 1 490 037, WO 01/15547, AU 2001279664, FR 2 350 105, U.S. Pat. No. 5,380,535, U.S. Pat. No. 3,037,911, describe how to encapsulate or coat one or more constituents and the techniques used.

These solutions require numerous encapsulation or coating steps, or have recourse to a production step such as extrusion which may degrade the fragile active substances or denature the constituents such as flavourings or palatable materials.

Another option to facilitate oral administration is to contain the composition, chiefly a medication, within a palatable material.

The following patent applications: FR 2 896 958, FR 2 715 803, U.S. Pat. No. 5,853,757, U.S. Pat. No. 6,143,316, U.S. Pat. No. 5,792,470, U.S. Pat. No. 5,674,515, EP 0 574 301, U.S. Pat. No. 4,857,333, DE 198 53 729, WO 03/030863, WO 2004/043427, WO 2007/090987, propose baits formed with palatable materials.

The disadvantage with these baits is that their use requires the handling namely the previous insertion of the medicine into the bait, which may deter some users and may also become tedious if a large number of animals are to be treated. In addition their large volume (necessarily larger than the medicinal product) requires a high amount of material and production must be adapted to their complex shape; these baits are therefore often costly.

A further option is to isolate the active substances in the centre of a matrix obtained by compressing the dry constituents, comprising a palatable substance to mask the taste and facilitate the taking and consumption thereof.

Patent application EP 0 320 320 describes a tablet for pet animal characterized in that it is formed of at least one core containing one or more active substances, fully contained within a matrix that is tasty for an animal. In such compositions it is the texture which amounts to the main drawback. A compressed or tablet form gives rise to hard forms scarcely appreciated by animals. In addition, the production of these types of core tablets entails numerous constraints to ensure full enclosing of the central part.

The following patent applications: EP 0 725 570, EP 0 725 627, propose compositions formed of two parts, a central part enclosing the constituents having an unpleasant taste and/or smell, and an outer part surrounding the central part. These are baits and the objective is to attract the animal so that by biting the composition the animal will be vaccinated. These have several disadvantages:

when forming the matrix, an increase in temperature to obtain the fusing of some constituents is necessary to melt the polymer so that it is closely mixed, which may be highly restrictive to obtain the stability of the active substance;

the producing of such matrixes is complex and costly;

storage requires special conditions to guarantee the integrity of the dosage form.

Patent application FR 2 709 420 describes a shape and size for a tablet so that it can be more easily grasped by animals, cats in particular.

The following patent applications: IE 2004 0393 and GB 2 432 506, describe palatable pet chews obtained by extrusion or extrusion moulding. The main disadvantage of these items is that they are consumed for several minutes, even abandoned and then picked up again to be re-chewed before being consumed. It is therefore not possible to follow a treatment schedule with certainty.

Patent application US 2011/0183036 describes pet treats obtained by extrusion moulding. The main drawback with these treats is that their production requires heat at a temperature higher than 82° C., from an extruded-moulded paste and there is hence lack of weight regularity. In addition, this paste contains water of which part, between 3 and 15%, remains in the treat after it has been formed. The application describes a treat and not a medicinal product.

U.S. Pat. No. 6,455,083 describes edible chews obtained by extrusion moulding. The main drawback is that they are thermoplastics i.e. polymerisation occurs in the extruder chiefly of the proteins with water (10 to 20%). Having regard to their texture, these items will not be absorbed at once but will be chewed with the risk of being abandoned. The patent describes nutritional chewable products and not medicinal products.

The following patent applications: FR 2 154 424, and U.S. Pat. No. 5,894,029 refer to the production of feed for pet animals. The production methods used are in no way adapted for the particular production of medicinal products. They may be highly harmful for the stability of the active substances, through the use of water in the formulas or processes, through the use of heat with or without pressure.

U.S. Pat. No. 5,637,313 describes special compositions, but more especially a particular method for obtaining coated tablets, namely the matrix after mixing is coiled into a cord of a certain diameter and cut to a certain length to obtain the desired weight. This production does not allow guaranteed full control over weight and hence over the quantity of active substance per unit, which is antinomic for a medicinal product.

Regarding texture, bearing in mind that it is strongly related to the composition and hence also to appetency, three main preparation methods have been proposed:

The first, the oldest, is dry compression to obtain tablets or pills. The patent applications already cited: EP 0 997 143, EP 1 490 037, EP 0 574 301, EP 0 320 320, U.S. Pat. No. 5,380,535, U.S. Pat. No. 3,037,911, FR 2 709 420 describe hard, dry forms scarcely appreciated by animals and numerous cases of rejection by animals have been reported.

The second, most recent, is the production of chewable tablets obtained by extrusion. For example the following patent applications: US 2004/0043925, US 2004/0037869, US 2001/036464, WO 2008/030469, WO 2005/013714, WO 89/12442, described extruded palatable forms having a relatively soft texture much appreciated by animals in particular pet animals such as dogs and cats. Having regard to the production mode, namely the use of an extruder, the matrix continually leaves the production line and is then cut to the desired length to obtain the required weight and hence a constant quantity of active substance(s) as required for a medicinal product. This requires perfect control over extrusion parameters. Unfortunately it is known that with this technique a variation in density of the extrudate cannot be ruled out which, at constant length, inevitably leads to a variation in weight. To overcome this possibility, the chewable tablets must be weighed one by one and those not conforming must be discarded since they cannot be recycled as the active substance may be modified by further extrusion. This technique proves to be in no way economical. To conclude, it would not be chosen by persons skilled in the art to produce a medicinal product or nutraceutical or food supplement in which the quantity of active substance(s) must be fully controlled.

Patent application US 2004/151759 describes chewable tablets obtained using conventional techniques: compressing dry granulated powder or extrusion with drying at 50° C. The two production methods have recourse to water for granulating, the water being removed before compression to obtain conventional tablets or after extrusion to obtain chewable tablets. These two techniques have the disadvantages already mentioned.

The third and last proposed is the production of soft tablets by moulding using equipment for pressing hamburgers, steaks, nuggets, cookies (before baking) (patty pressing machines). For example, the following patent applications: US 2005/0226908 and the patent applications in the same family, WO 2009/064859 and U.S. Pat. No. 7,955,632, U.S. Pat. No. 8,293,265, WO 2012/049156, U.S. Pat. No. 8,114, 455 and US 2012/0141574 describe chewable tablets obtained by moulding a paste with little or no pressure (explicit in applications WO 2009/064859, U.S. Pat. No. 7,955,632, U.S. Pat. No. 8,293,265, U.S. Pat. No. 8,114,455, US 2012/0141574), prepared with water (application WO 2012/049156) or in the presence of water (application US 2005/0226908), the use of heat (applications US 2005/

0226908, WO 2012/049156) all the applications recommending the same equipment by Formax Corporation: Formax F6™. Having regard to the production mode, namely the use of patty pressing machines which are fed with a paste which may be homogeneous but is of random density leading to a random moulded amount and hence to a random amount of active substance(s) not compatible with a medication. This requires full control over the physical characteristics of the paste. Unfortunately it is known that a variation in density cannot be ruled out with a scarcely fluid paste since it is cold moulded. In addition to this disadvantage is that of the system for feeding the moulds which aerates the paste, which inevitably leads to a variation in the weight of the tablets. To overcome this problem the chewable tablets must be weighed one by one, those not conforming not able to be recycled as the supply of active substance may be modified by further forming. This technique proves to be in no way economical. To conclude, it would not be chosen by persons skilled in the art to produce a medication or nutraceutical or food supplement for which the quantity of active substance(s) must be fully controlled.

The applicant has therefore set itself the objective of remedying the disadvantages of the prior art by developing compositions and determining a process with which it is possible to impart homogeneity to the compositions and stability over time of the active substance or substances, for administration in solid form having a pleasant texture and improved appetency for animals. In particular the applicant has endeavoured to develop a veterinary composition for simple oral administration adapted to and appreciated by every animal species, that is economical and whose production can easily be given industrial application, the quantity of each component being fully controlled in particular the active substance(s) if it is a medicinal product or nutraceutical or food supplement.

During the work which led to the development of the palatable composition of the invention, the applicant found that the obtaining of this palatable composition containing a maximum amount of palatable matter using a compression technique for formulas having high fat content, led to veterinary compositions in solid form for oral administration containing one or more active substances consumed in whole by all animal species. With this technique it is possible to choose a composition that is fully adapted and hence appreciated by each targeted animal species, by proper selection of the formula components, the majority of which are sought to be palatable, the texture and shape and size being particular to the targeted animal species. With this technique it is also possible to select components for the composition that do not cause instability in particular degradation of the active substance or substances. In addition, it was surprisingly discovered that if the active substance(s) were added last to the mixture, this made it possible to better preserve their integrity and stability throughout the storage period of the solid form. This technique allows the production of very homogeneous compositions and guarantees with much accuracy the quantity of active substance(s) contained therein at the time of manufacture and over time. In addition, this technique is most economical and can easily be given industrial application.

The invention relates to a process for manufacturing a solid composition, stable over time and containing an accurate dose of active substance, to this composition and to the use thereof in particular as palatable composition for oral administration to animals, wherein the active substance(s) are included at the last preparation step via addition to a granulate previously obtained with all the other components (these other components advantageously not comprising any active substance). At the time the active substance(s) and advantageously all the active substance(s) are added, the granulate is advantageously cold i.e. it is at ambient temperature which may vary from 15° C. to 30° C., advantageously 15° C. to 25° C. and it does not contain any water.

By "stable over time" it is meant that after a composition storage time of at least one year at 25° C. (±5° C.) under relative humidity conditions varying from 30 to 70%, the mixture remains homogeneous since the dosage values of active substance all remain within the dose range. The dose range corresponds to the target dose±5%, the percentages being expressed by weight.

The compositions have a texture, shape and size pleasing to animal species. The present composition is advantageously in the shape of an accurately dosed cube that is stable over time, palatable, well accepted by all animals irrespective of species and rapidly absorbed whether given occasionally or on a repeat basis.

The description of the invention is given below and is based in particular on examples given solely as illustrations and with reference to the appended Figures in which.

More particularly, the subject of the invention is a process for preparing a palatable, solid composition stable over time, characterized in that the composition comprises:

α. 3 to 30%, preferably 5 to 15% by weight of at least one fatty substance selected from among a fat or wax or liquid oil, a thickened liquid oil or a mixture thereof, the liquid oil of the liquid or thickened oil not representing more than 8% by weight of the composition;

β. 0.001 to 57% by weight of at least one active substance;

χ. 40 to 96.999% by weight of at least one palatable material, when the active substance is also a palatable material, the content of active substance may range up to 97% by weight, advantageously up to 85% by weight and, as palatable material, the composition may comprise only this active substance or a mixture of the active substance with at least one other palatable material;

δ. optionally one or more additives advantageously selected from among fillers, binders, solvents, absorbent/gelling substances, flavourings, surfactants, taste enhancers, sweeteners, antioxidants, colouring agents and pH regulators.

a) the liquid or thickened oil is selected from among olive oil, groundnut oil, rapeseed oil, sunflower seed oil, the triglycerides of capric and caprylic acids, the propylene glycol of dicapric/dicaprylic acids and the mixtures thereof;

b) the fat is selected from among chicken fat, duck fat, lard, suet, butter, palm fat, palm stearin, margarine, optionally hydrogenated palm oil, cetyl palmitate, hydrogenated coconut oil, the triglycerides of capric, caprylic, myristic and stearic acids, and the mixtures thereof;

c) the wax is selected from among beeswax, carnauba wax, candelilla wax, and the mixtures thereof;

d) the palatable material is selected from among meat, meat powder, fish powder, cheese powder, milk derivatives, liver powder, the extracts of these animal substances or the derivatives thereof; beer yeast; vegetable fibres; vegetable products or by-products such as fenugreek, apple, carrot, fodder beet, sugar beet, thyme, alfalfa, sugar cane, and cereals such as oats, wheat, rice, corn, soy, their derivatives e.g. flours and mixtures thereof; sugar (sucrose) in all its forms, granulated, caster, icing, glucose, invert sugar, molasses, honey or its derivatives; and the mixtures thereof; salt (sodium chloride), and the mixtures thereof;

e) the solid palatable composition has a unit weight to within 3% of the theoretical value of the required weight, and preferably to within 2% of the theoretical value of the required weight;

f) the solid palatable composition is stable for more than one year when stored at ambient temperature;

and in that the process comprises the following successive steps:

i) preparing a homogeneous granular material comprising or advantageously consisting of the palatable material(s), fatty substance and optionally one or more additives;

ii) under agitation and at ambient temperature, without the addition of water or the application of heat, adding the active substance(s) advantageously all the active substances to the cold granular material obtained after step i);

iii) calibrating the dry, fluid granular mixture obtained after step ii) to retain the granules having a particle size of between 50 and 1000 µm, preferably between 200 and 800 µm, more preferably between 200 and 600 µm;

iv) compressing the dry, fluid, calibrated granules obtained after step iii) using a press for compressing formulas having a high fat content;

v) collecting the solid, palatable composition after step iv).

The fatty substance is advantageously in solid, waxy or paste form.

Step i) advantageously comprises the following successive steps:

i1) mixing the palatable material(s) and optionally one or more additives, the palatable materials and optional additives being in powder form;

i2) Adding the fatty substance to the mixture obtained after step i);

i3) Mixing or triturating without the addition of water or application of heat until a homogenous granular material is obtained.

It is preferable that at step i1) the palatable materials and optional additives should have a particle size of less than 200 µm, advantageously less than 100 µm. Mixing can be carried out in a mixer-granulator.

According to one preferred embodiment, the fat is in solid, waxy, paste or thickened liquid form.

To ensure the stability of the compositions obtained, the active substance(s) are added once the other components, advantageously all the other components have been mixed and granulated. When adding the active substance(s), the granular material of step iii) is cold and does not contain any water. By "cold" it is meant that it is at ambient temperature i.e. between 15° C. and 30° C., advantageously between 15° C. and 25° C. By "does not contain any water" it is meant that the water content is lower than 5% by weight relative to the total weight of the granular material. The said active substances may be in the form of:

powders, or solubilised in a suitable non-aqueous solvent to be vaporised or poured onto the granular material of step i), or solubilised in a suitable, non-aqueous solvent then converted to a gel or powder by adding an absorbent substance, or in granule form after a coating operation for example.

The active substance(s) may be simply distributed as a powder within the edible cube, or they may previously vaporised onto all or part of the granular material after being solubilised in a suitable non-aqueous solvent, or converted to a solid after gelling of a solution, or granulated or coated using techniques known to those skilled in the art so as not to modify their bioavailability or so as to increase masking of their smell or taste vis-à-vis the olfactory or taste senses of the animal.

When in powder form, the active substance advantageously has a particle size of less than 200 µm, advantageously less than 100 µm.

When in the form of granular material, the active substance advantageously has a particle size that at the most is equivalent to the size of the granular material at step iii), having a particle size of between 50 and 1000 µm, preferably between 200 and 800 µm, more preferably between 200 and 600 µm.

Step ii) is advantageously performed without the application of heat or addition of water.

Figure 1:
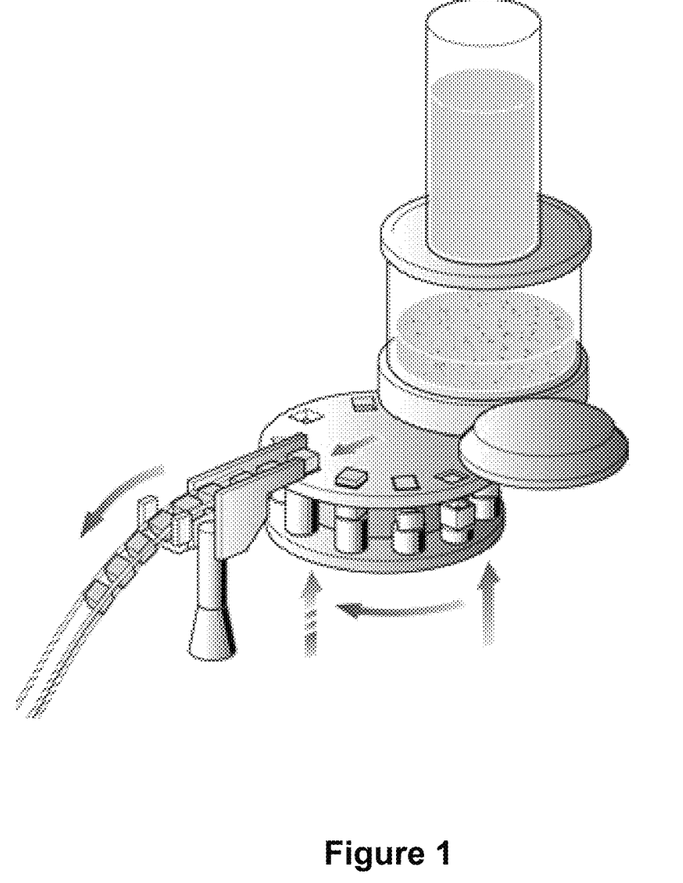
FIG. 1 is a schematic illustration of a press for the compression of formulas with high fat content and FIG. 2 is a schematic illustration of a cluster-breaker-size grader advantageously mounted on the feed vessel of the press for the compression of formulas with high fat content.
Figure 2:
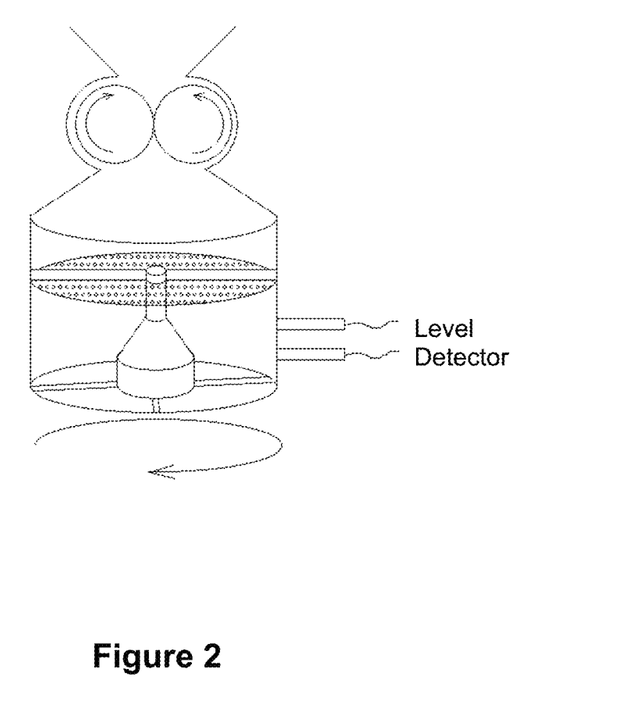

The homogeneous mixture is then calibrated to obtain a particle size of between 50 and 1000 µm, preferably between 200 and 800 µm, more preferably between 200 and 600 µm. The fluid, calibrated mixture is then compressed using standard equipment such as presses used to compress formulas having a high fat content by Fette, Bonals, IMA or Corazza (FIG. 1: schematic of the operating principle of the press) giving compact, homogeneous masses. The said equipment is advantageously modified:

by adding a cluster breaker/size grader to the feed vessel of the press for compressing formulas with high fat content, which will allow improved filling of the alveolus with a constant volume i.e. the volume of the granular material, hence the weight placed in the alveolus is as constant as possible to guarantee a very small variation in weight of the resulting edible/chewable cube relative to the fixed theoretical weight, with the consequence that the quantity of active substance contained in the cube will be fully constant (FIG. 2: cluster breaker/size grader); and to improve extraction of the edible/chewable cube, but also to prevent any heating which could be detrimental to the stability of the cube/active substance, the compression stage is chilled.

Therefore the press for compressing formulas with high fat content is advantageously equipped with a cluster breaker-size grader and/or a chilled compression stage.

At step iv) the compression force is advantageously between 5 and 80 kN, more advantageously between 20 and 60 kN, further advantageously between 35 and 45 kN. The compression step is advantageously conducted at ambient temperature i.e. between 15° C. and 30° C., advantageously between 15° C. and 25° C.

The palatable composition obtained is advantageously in the form of a compact mass, at least the top and bottom surfaces being planar. Advantageously the composition is in the form of a cube or parallelepiped the side of which advantageously varies from 10 mm to 40 mm, more advantageously from 12.5 mm to 35 mm (depending in particular on the mammal for which the composition is intended). The process of the invention allows compositions to be obtained having a very homogeneous unit weight not differing by more than 3% from the theoretical value of the required weight and preferably not more than 2% from the theoretical value of the required weight.

The compositions of the present invention are typically in the form of edible/chewable cubes used to facilitate oral administration to animals, preferably mammals. Even if the palatable composition in solid form for oral administration to animals is designated as being an "edible/chewable cube", other forms can be envisaged paying heed to the constraints of the equipment, namely at least the top and bottom surfaces of the edible/chewable cube are planar.

The hardness of the edible/chewable cubes can be controlled by adjusting the pressure applied by the press for compressing formulas with high fat content and by adjusting the formula of the composition.

The compositions or "edible/chewable cubes" of the present invention are obtained via compression using a press to compress formulas having high fat content, excluding any and all equipment operating continuously such as by extrusion or which include a continuous production step such as extrusion-moulding, or which are fed with a pasty or heterogeneous mixture such as equipment for compressing hamburgers with or without the presence of heat or moisture.

The compression technique using a press for compressing formulas having high fat content is widely used in the human food sector as evidenced by the following patent applications: U.S. Pat. No. 6,126,979, WO 2004/112513, WO 2006/063694, WO 2007/085609, WO 2009/068378, OA 12967 describing compositions and the use of compression to form stock cubes or stock tablets. The latter cannot be used directly and must first be dissolved in water or an aqueous vehicle that is preferably hot or at least tepid. In addition, these stock cubes are very friable since it must be possible to crumble them easily into food preparations. On this account, persons skilled in the art would not be prompted to use these formulations and their method of production to obtain a solid palatable composition having the desired texture.

The compression technique for compressing formulas with high fat content is known in the prior art and is notably used in the human food sector. These products are typically stock cubes. However the compositions obtained using this process for compressing formulas having high fat content have never been used up until now in the veterinary field i.e. given directly to animals, more particularly to mammals via direct oral administration, with the exception of man in whom they are consumed indirectly either dissolved in hot or tepid water or crumbled into food preparations before cooking.

Nor was it taught that the stability of the compositions could be improved by adding the active substance(s) to the other components, advantageously all the other components previously mixed and granulated.

Compared with other techniques for manufacturing products to be given orally to animals described in the prior art, which particularly include the compression of dry powder, extrusion and moulding, the compression of formulas with high fat content allows products to be obtained which have a higher content of fatty substance and palatable material leading to full appetency i.e. total ingestion by animals even on a repeat basis. All the compositions contain an active substance, this compression method providing full control over the weight of the edible/chewable cube and hence over the quantity of active substance contained in each unit of the end product, thereby guaranteeing compliance with therapeutic treatment.

In the prior art methods:
the compression of dry powder does not allow the obtaining of products sufficiently high in palatable materials, having a texture appreciated by animals;
the extrusion and extrusion-moulding methods do not allow products to be produced that are sufficiently high in non-exuding fat, whilst obtaining perfect product dosage;
the methods for moulding hamburgers do not allow products to be obtained that are sufficiently high in non-exuding fat whilst obtaining perfect product dosage.

Therefore, the products obtained by extrusion or moulding in particular generally have strong variations in weight. These variations are due to different factors such as the feeding of mixture to the equipment, but also the mixture itself in a paste formed in the screws of the extruder, or formed directly for moulding, this paste being highly heterogeneous. These variations can be offset by sorting the products leaving the production lines, but such sorting is associated with major loss of product leading to non-negligible additional costs. The calibration of the products is particularly determinant for compositions incorporating an active substance. To allow the administering of a constant quantity of active substance, the end product must be perfectly calibrated regarding weight. This calibration is advantageously obtained when producing the compositions of the present invention by compressing formulas having a high fat content.

Comprising one or more active substances, the solid, palatable compositions obtained are advantageously used for administration to animals for therapeutic treatment, either medicinal or nutraceutical or as food supplement, the animals more particularly being mammals.

By "active substance" is meant a medicinal, nutraceutical or food supplement substance having a therapeutic effect or biological activity.

The active substance content is adapted in the composition in relation to the selected active ingredient and the animal to be treated.

The amount of active substance per solid composition is dependent on its efficacy. For example it may be very low, in the region of a few tens of micrograms up to several grams.

The minimum content of active substance(s) expressed by weight relative to the total weight of the composition may be at least 0.001% or at least 0.01% or at least 0.1% or at least 1%.

A solid composition may contain a single active substance or a combination of active substances. The total content of active substance(s) varies from 0.001 to 57% by weight, advantageously from 0.001 to 50% by weight, more advantageously from 0.001 to 40% by weight or 0.001 to 30% by weight.

However, these ranges may differ when one of the active substances is a palatable substance at the same time. The active substance may effectively also be a palatable material allowing a content thereof of up to 97% by weight, advantageously up to 85% by weight.

Preferably the active medicinal substance is selected from among anti-infectives such as antibiotics and sulfonamides, cardiotonics; internal and external anti-parasitics; insecticides; insect growth inhibitors; anti-arthritics; anti-inflammatories whether or not steroidal; anti-histaminics; hormones such as prostaglandins; digestive therapy substances such as gastro-intestinal dressings and sedatives; anti-ulcer drugs and substitution flora; anti-diarrhoeals; hepato-protectors; antispasmodics; laxatives; intestinal antiseptics; substances for respiratory therapy such as respiratory analeptics; antitussives, broncho-dilatators, bronchial and mucolytic fluidifiers; substances acting on the nervous system such as analgesics, sedatives and tranquillisers; antiepileptics; anaesthetics; orexigenics; anorexigenics; substances for immunity therapy such as interleukins and interferon in particular; substances for anticancer therapy such as antimitotics and cytostatics; macro-, micro-nutrients and trace elements; vitamins; extracts of plants or animal organs; and the mixtures thereof.

In one advantageous embodiment, the active substance is selected from among antibiotics such as amoxicillin, clavulanic acid, cephalexin, rifaximin; anti-parasitics such as ivermectin, moxidectin, milbemycin pyrantel and its derivatives such as the pamoate, praziquantel, benzimidazoles, their salts or derivatives; insecticides such as fampronil; cardiotonics such as levosimendan; anti-arthritics such as diacerein.

Preferably the active nutraceutical or food supplement substance is selected from among extracts of plants or animal organs for their anti-infectious, antibacterial, anti-fungal, anti-diarrhoeal, hepato-protector, anti-spasmodic, laxative, intestinal anti-septic activity; for their activity on respiratory problems such as coughs, as bronchodilators, bronchial and mucolytic fluidifiers, respiratory anti-septic, analgesic, sedative, tranquilliser, anti-arthritic, insecticidal, anti-parasitic, anti-ulcer, anti-stress agents; and substitution flora; macro, micro nutrients and trace elements; vitamins, and the mixtures thereof.

In one advantageous embodiment, the active nutraceutical or food supplement substance is selected from among extracts of plants or animal organs for their anti-arthritic action such as chrondroitin sulfate acid, chitosan and its derivatives; for their anti-ulcer and/or anti-stress action such as fermented soy extract; for their insecticidal or insect repellent action such as pyrethrums; vitamins such as vitamin C, vitamin D3; substitution flora such as *Enterococcus faecium*; micronutrients such as selenium provided by a strain of *Saccharomyces cerevisiae*.

It will be understood that an active substance may have several functions; for example fermented soy extract may be both an active substance and a palatable material.

The compositions of the present invention comprise at least one palatable ingredient in high quantity contributing towards the organoleptic characteristics of the composition according to the invention and its appetency for animals.

The content of palatable material is advantageously at least 40% by weight, more advantageously at least 50% by weight, even further advantageously at least 60% by weight relative to the total weight of the composition. The composition may comprise up to 96.999% by weight, advantageously up to 90% by weight of palatable material.

When the palatable material is also the active substance, the content of palatable material may be 97% by weight.

Palatable materials for targeted animals are substances of animal or vegetable origin for example, powdered directly after treatment such as drying or dehydration, grinding, calibrating, but also after processing with the addition of other components to promote preservation for example. The palatable components are selected from among substances of choice which are highly tasty for the targeted species, in particular carnivorous pet animals such as dogs and cats and herbivorous animals e.g. horses.

In the uses and compositions of the invention, the palatable material is selected either from the animal kingdom or from the vegetable kingdom depending on the targeted animal species, preferably from among meat, meat powders, fish powders, cheese powders, milk derivatives, liver powder, the extracts of these animal substances or their derivatives; beer yeast; vegetable fibres; vegetable products or by-products such as fenugreek, apple, carrot, fodder beet, sugar beet, thyme, alfalfa, sugar cane, and cereals such as oats, wheat, rice, corn, soy, their derivatives such as flours and the mixtures thereof; sugar (sucrose) in all its forms—granulated, caster, icing, glucose, invert sugar, molasses, honey or its derivatives; and the mixtures thereof; or in the mineral kingdom, salt (sodium chloride).

It will be understood that any component in the formulation may also be a palatable material for animals.

The compositions of the present invention comprise at least one fatty substance.

The content of fatty substance is at least 3% by weight relative to the total weight of the composition, advantageously at least 5% by weight, more advantageously at least 10% by weight. The content of fatty substance in the composition expressed by weight relative to the total weight of the composition may range up to 30% or lower, advantageously up to 20%, more advantageously up to 15%.

By "fatty substance" is meant a material containing one or more lipids.

By "fat" is meant a substance mostly containing triglycerides.

In the uses and compositions of the invention, the fat is preferably selected either in the animal kingdom or in the vegetable kingdom depending on the targeted animal species, from among pasty or hard fats, chicken fat, duck fat, lard, suet, butter, palm fat, palm stearin, margarine, palm oil optionally hydrogenated, cetyl palmitate hydrogenated coconut oil, the triglycerides of capric, caprylic, myristic and stearic acids, and the mixtures thereof.

By "waxes" is meant waxes permitted in food and in particular in animal foods.

In the uses and compositions of the invention, the wax is preferably selected either in the animal kingdom or in the vegetable kingdom depending on the targeted animal species, from among beeswax, carnauba wax, candelilla wax, and the mixtures thereof.

By "oil" is meant a fatty substance which is liquid at ambient temperature. In general the oil is of vegetable origin although it may be of animal or mineral origin. Depending on the targeted species, preference is given to oils of vegetable or animal origin.

According to the invention the edible/chewable cube may contain an acceptable liquid oil having no degrading action on the other selected components, in particular the active substance.

In the uses and compositions of the invention, the liquid or thickened oil is preferably selected from among olive oil, groundnut oil, rapeseed oil, sunflower seed oil, the triglycerides of capric and caprylic acids, the propylene glycol of dicapric/dicaprylic acids, and the mixtures thereof.

In the uses and compositions of the invention, the fats or waxes or thickened oils will allow granulation of the powder components to arrive at a homogeneous mixture.

It will be understood that a thickened oil, a fatty substance, a wax may also be palatable materials for animals.

The composition further comprises one or more additives preferably selected either from the animal kingdom or from the vegetable kingdom depending on the targeted animal species, from among fillers, binders, solvents, absorbent/gelling substances, flavourings, surfactants, taste enhancers, sweeteners, antioxidants, chelating agents, preserving agents, colouring agents and pH regulators.

Preferably the filler is chosen from among maltodextrins; cyclodextrins; lactose; talc; silicates; phosphates, cellulose powder; microcrystalline cellulose; mica and carbonates.

Advantageously, when present the filler represents 1 to 25% by weight of the composition relative to the total weight of the composition.

The compositions of the invention comprise at least one binder. Advantageously the binder is selected from among polyvinyl alcohol polymers, polyvinylpyrrolidone, the copolymers of vinylpyrrolidone and vinyl acetate, carboxymethylcellulose, its salts and derivatives, solid polyethylene glycols and the derivatives thereof, gelatines, alginic acid and its salts, zein, pectins, gum arabic, acacia gum, gum tragacanth, karaya gum, xanthan gum, carrageenans, pullulan polymers, agar polymers, starches and the derivatives thereof, sugars and the derivatives thereof such as molasses, carbomers, acrylic acid cross-linked with polyalkenyl ethers, polycarbophils, and the mixtures thereof. Advantageously, when present, the binder represents 1 to 25% by weight of the composition relative to the total weight of the composition.

Preferably, the solvent is selected from among ethanol, propylene glycol, glycerine, cetyl alcohol, benzyl alcohol, liquid polyethylene glycols and the mixtures thereof. Advantageously when present the solvent represents 1 to 25% by weight of the composition relative to the total weight of the composition.

Preferably, the absorbent/gelling substance is selected from among stearic acid, the derivatives and salts thereof such as glyceryl stearates, aluminium or magnesium stearates, hydrogenated castor oil, bentonite, silica derivatives such as colloidal silica, precipitated silica, pyrogenated silica, cellulose and the derivatives thereof such as methyl or ethyl cellulose, hydroxypropylcellulose, hydroxypropylmethylcellulose, spray-dried whey, starches, and the mixtures thereof. Advantageously, when present, the absorbent/gelling substance represents 0.1 to 10% by weight of the composition relative to the total weight of the composition.

A flavouring is an odorous ingredient of a certain substance (of synthetic or natural origin) which is only perceived by the sense of smell. It does produce any sensation on the organ of taste and therefore has no taste. Advantageously, when present, the flavouring represents 0.01 to 5% by weight of the composition relative to the total weight of the composition.

Preferably, the flavouring is selected from among essential oils, terpene derivatives such as menthol, and the mixtures thereof.

Preferably, the surfactant is selected from among glycol esters such as glycerol monostearate, the esters of fatty acid and sorbitan, the esters of polyoxyethylenated fatty acids and sorbitan; polyoxyethylenated vegetable oils such as polyoxyethylenated castor oils, polyoxyethylenated hydrogenated vegetable oils such as polyoxyethylenated hydrogenated castor oil; lecithin and its soy or egg derivatives such as phosphatidylcholine, hydrogenated phosphatidylcholine, lysophosphatidylcholine, hydrogenated lysophosphatidylcholine, and the mixtures thereof. Advantageously, when present, the surfactant represents 0.1 to 10% by weight of the composition relative to the total weight of the composition.

In one preferred embodiment, the taste enhancer is sodium glutamate. Advantageously, when present, the taste enhancer represents 0.1 to 10% by weight of the composition relative to the total weight of the composition.

In one preferred embodiment, the sweetener is selected from among aspartame; sodium saccharin; thaumatin; polyols such as sorbitol, xylitol, isomalt, maltitol, mannitol, and lactitol; and the mixtures thereof. Advantageously when present, the sweetener represents 0.1 to 10% by weight of the composition relative to the total weight of the composition.

Preferably the antioxidant is selected from among ascorbic acid, its salts and derivatives, sodium or potassium metabisulphite, sodium bisulphite, butylhydroxyanisol, butylhydroxytoluene, gallic acid and its derivatives such as propyl gallate, and the mixtures thereof. Advantageously, when present, the antioxidant represents 0.01 to 5% by weight of the composition relative to the total weight of the composition.

Preferably, the chelating agent is selected from among EDTA and its salts, tartaric acid and its salts, and the mixtures thereof. Advantageously, when present, the chelating agent represents 0.01 to 5% by weight of the composition relative to the total weight of the composition.

Preferably, the preserving agent is selected from among parabens, benzoic acid and its salts, sorbic acid and its salts, and the mixtures thereof. Advantageously, when present, the preserving agent represents 0.01 to 5% by weight of the composition relative to the total weight of the composition.

Preferably, the colouring agent is selected from among iron oxides titanium oxide, curcumin, caramel, carotenes, and the mixtures thereof. Advantageously, when present, the colouring agent represents 0.1 to 5% by weight of the composition relative to the total weight of the composition.

Preferably, the pH regulator is selected from among citric acid, its salts and derivatives, sodium carbonates, delta glucono lactone, and the mixtures thereof. Advantageously, when present, the pH regulator represents 0.1 to 10% by weight of the composition relative to the total weight of the composition.

In one preferred embodiment, the additive(s) represent 0.01 to 25%, preferably 0.1 to 15% by weight of the composition relative to the total weight of the composition. In another variant, the additives represent 0.01 to 56.999%, preferably 0.1 to 47% by weight of the composition relative to the total weight of the composition.

It will be understood that a filler may have several functions, therefore a vegetable product or by-product such as cereal powder or sugar may be both an inert filler and a palatable material.

A further subject of the invention is a solid, palatable composition that is stable over time and can be obtained using the process according to any of the claims, characterized in that the composition comprises:

α. 3 to 30%, preferably 5 to 15% by weight of at least one fatty substance advantageously in solid, wax or paste form selected from among a fat or wax or liquid oil, a thickened liquid oil, or a mixture thereof, the liquid oil or the liquid oil of the thickened oil not to represent more than 8% by weight of the composition;

β. 0.001 to 57% by weight of at least one active substance; and

χ. 40 to 96.999% by weight of at least one palatable material;
when the active substance is also a palatable material the content of active substance may range up to 97% by weight, advantageously up to 85% by weight and the composition, as palatable material, may comprise this sole active substance or a mixture of the active substance with at least one other palatable material, δ. optionally one or more additives advantageously selected from among fillers, binders, solvents, absorbent/gelling substances, flavourings, surfactants, taste enhancers, sweeteners, anti-oxidants, chelating agents, preserving agents, colouring agents and pH regulators;

a) the liquid oil is selected from among olive oil, groundnut oil, rapeseed oil, sunflower oil, the triglycerides of capric and caprylic acids, the propylene glycol of dicapric/dicaprylic acids, and the mixtures thereof;
b) the fat is selected from among chicken fat, duck fat, lard, suet, butter, palm fat, palm stearin, margarine, palm oil optionally hydrogenated, cetyl palmitate, hydrogenated coconut oil, the triglycerides of capric, caprylic, myristic and stearic acids, and the mixtures thereof;
c) the wax is selected from among beeswax, carnauba wax, candelilla wax, and the mixtures thereof;
d) the palatable material is selected from among meat, meat powders, fish powders, cheese powders, milk derivatives, liver powder, extracts of these animal substances or their derivatives; beer yeast; vegetable fibres; vegetable products or by-products such as fenugreek, apple, carrot, fodder beet, sugar beet, thyme, alfalfa, sugar cane, and cereals such as oats, wheat, rice, corn, soy, the derivatives thereof such as flours, and the mixtures thereof; sugar (sucrose) in all forms—granulated, caster, icing, glucose, invert sugar, molasses, honey or its derivatives, and the mixtures thereof, salt (sodium chloride), and the mixtures thereof.
e) the solid, palatable composition has a unit weight to within about 3% of the theoretical value of the required weight, and preferably to within about 2% of the theoretical value of the required weight;
f) the solid, palatable composition is stable for more than one year when stored at ambient temperature.

The composition and the components thereof, in particular their content, are such as previously described.

Advantageously the composition is formed of:
a) at least one medicinal active substance selected from among antibiotics such as amoxicillin, clavulanic acid, cephalexin, rifaximin; anti-parasitics such as ivermectin, moxidectin, milbemycin pyrantel and its derivatives such as the pamoate, praziquantel, benzimidazoles, their salts or derivatives; insecticides such as fampronil; cardiotonics such as levosimendan; anti-arthritics such as diacerein; a nutraceutical active substance of food supplement selected from among animal extracts for their anti-arthritic action such as chondroitin sulfate, chitosan and its derivatives, for their anti-ulcer and/or anti-stress action such as fermented soy extract; for their insecticide action such as pyrethrums, vitamins such as vitamin C, vitamin D3; substitution flora such as *Enterococcus faecium*; micro-nutrients such as selenium provided by a strain of *Saccharomyces cerevisiae*;
b) at least one fatty substance selected from among from among chicken fat, duck fat, lard, suet, butter, palm fat, palm stearin, margarine, palm oil optionally hydrogenated, cetyl palmitate hydrogenated coconut oil, and the mixtures thereof; waxes such as beeswax, carnauba wax, candelilla wax, and the mixtures thereof; oils such as olive oil, groundnut oil, rapeseed oil, sunflower seed oil, the triglycerides of capric and caprylic acids and their derivatives, or the mixtures thereof;
c) at least one palatable material selected from among meat, meat powder, fish powder, cheese powder, milk derivatives, liver powder, gelatine, the extracts of these animal substances or the derivatives thereof; beer yeast; vegetable fibres; vegetable products or by-products such as fenugreek, apple, carrot, fodder beet, sugar beet, thyme, alfalfa, sugar cane, and cereals such as oats, wheat, rice, corn, soy, their derivatives e.g. flours and mixtures thereof; sugar (sucrose) in all its forms, granulated, caster, icing, glucose, invert sugar, molasses, honey and its derivatives, and the mixtures thereof, salt (sodium chloride), and the mixtures thereof.

The content of active substance is adapted in the composition in relation to the selected active ingredient and animal to be treated. This content may vary from 0.001 to 97% by weight relative to the total weight of the composition, advantageously 0.001 to 57% by weight, more advantageously from 0.001 to 50% by weight, further advantageously 0.001 to 40% by weight or 0.001 to 30% by weight if the active substance is not a palatable substance at the same time.

The content of fatty substance is at least 3% by weight relative to the total weight of the composition, advantageously at least 5% by weight, more advantageously at least 10% by weight. The content of fatty substance in the composition, expressed by weight relative to the total weight of the composition, may range up to 30% or less, advantageously up to 20%, more advantageously up to 15%.

The content of palatable material is advantageously at least 40% by weight, more advantageously at least 50% by weight, even further advantageously at least 60% by weight relative to the total weight of the composition. The composition may comprise up to 96.999%, advantageously up to 90% by weight or 97% by weight of palatable material if the palatable material is also the active substance.

The composition can be used:
- as medicinal product for mammals, except man, in particular for domestic animals such as dogs, cats or horses; or
- as nutraceutical or food supplement for mammals, except man, in particular for domestic animals such as dogs, cats or horses.

Finally, the subject of the invention is a solid, palatable composition characterized in that the composition comprises:
α. 3 to 30%, preferably 5 to 15% by weight of at least one fatty substance advantageously in solid, wax or paste form selected from among a fat or wax or liquid oil, or a thickened liquid oil, or a mixture thereof, the liquid oil or the liquid oil of the thickened oil not to represent more than 8% by weight of the composition;
β. 0.001 to 57% by weight of at least one active substance;
χ. 40 to 96.999% by weight of at least one palatable material;
when the active substance is also a palatable material the content of active substance may range up to 97% by weight, advantageously up to 85% by weight and the composition, as palatable material, may comprise this sole active substance or a mixture of the active substance with at least one other palatable material;
δ. optionally one or more additives advantageously selected from among fillers, binders, solvents, flavourings, surfactants, taste enhancers, sweeteners, antioxidants, chelating agents, preserving agents, colouring agents and pH regulators.

a) the liquid oil is selected from among olive oil, groundnut oil, rapeseed oil, sunflower oil, and the mixtures thereof;
b) the fat is selected from among chicken fat, duck fat, lard, suet, butter, palm fat, palm stearin, margarine, palm oil optionally hydrogenated, cetyl palmitate, hydrogenated coconut oil, and the mixtures thereof;
c) the wax is selected from among beeswax, carnauba wax, candelilla wax, and the mixtures thereof;
d) the palatable material is selected from among meat, meat powders, fish powders, cheese powders, milk derivatives, liver powder, extracts of these animal substances or their derivatives; beer yeast; vegetable fibres; vegetable products or by-products such as fenugreek, apple, carrot, fodder beet, sugar beet, thyme, alfalfa, sugar cane, and cereals such as oats, wheat, rice, corn, soy, the derivatives thereof such as flours, and the mixtures thereof; sugar (sucrose) in all forms—granulated, caster, icing, glucose, invert sugar, molasses, honey or its derivatives, and the mixtures thereof, salt (sodium chloride), and the mixtures thereof;

e) the solid, palatable composition has a unit weight to within 3% of the theoretical value of the required weight, and preferably to within 2% of the theoretical value of the required weight;

f) advantageously the solid, palatable composition is stable for more than one year when stored at ambient temperature;

for use thereof as medicinal product, nutraceutical or food supplement, for oral administration to mammals, except man, in particular for domestic animals such as dogs, cats or horses.

In one variant the composition comprises:

- 5 to 30%, preferably 8 to 20% by weight of at least one fatty substance selected from among liquid oil, a thickened oil, a fat or wax or mixture thereof, the liquid oil not to represent more than 8% by weight of the composition;
- 0.001 to 85% by weight of at least one active substance; and
- 20 to 95% by weight, advantageously 20 to 90%, preferably 40 to 70% by weight of at least one palatable material.

According to one preferred embodiment, the fatty substance is in solid, waxy, paste or thickened liquid form.

The additive may also comprise or consist of absorbent/gelling substances.

The liquid or previously thickened oil may also be selected from among the triglycerides of capric and caprylic acids, the propylene glycol of dicapric/dicaprylic acids and the mixtures thereof with the other possibilities.

The fat can also be selected from among the triglycerides of capric, caprylic, myristic and stearic acids, and the mixtures thereof with the other possibilities.

The solid, palatable composition is advantageously able to be obtained using the process of the invention.

The examples are to be construed solely as illustrations of the subject of the invention and are in no way limiting.

EXAMPLE 1—PREPARATION OF EDIBLE/CHEWABLE CUBES FOR DOGS

Edible/chewable cubes of 1.1 g containing 2.5 mg of milbemycin, 12.5 mg of praziquantel were prepared using the following composition:

| | |
|---|---|
| Milbemycin | 0.227% |
| Praziquantel | 1.136% |
| Liver powder | 46.00% |
| Glycerine | 18.00% |
| PEG 4000 | 12.00% |
| Gelatine | 8.00% |
| Sugar | 8.582% |
| Glycerol distearate | 5.00% |
| Propylene glycol of dicapric/dicaprylic acids | 1.00% |
| BHA | 0.04% |
| Propyl gallate | 0.01% |
| Precipitated silica | 0.005% | a) Batch of Cubes Produced According to the Invention

In a mixer, mix add the liver powder and glycerol distearate and mix. Add the PEG 4000, BHA, propyl gallate and continue mixing. Add the gelatine, sugar and mix. Pour the glycerine onto the homogeneous mixture. Mix until a dry, fluid, homogeneous granular material is obtained. Dissolve the milbemycin in the propylene glycol of dicapric/dicaprylic acids and add the precipitated silica to thicken the solution. Add the praziquantel to one tenth of the granular material and mix. Add the thickened solution of milbemycin and mix until a homogeneous mixture is obtained. Add the remainder of the granular material in small amounts whilst continuing to mix. Calibrate the granular material through a 800 μm mesh screen. Edible/chewable cubes of parallelepiped shape and measuring 12.5×12.5×7.0 mm are obtained by compression at 40 kN using a press for compressing formulas with high fat content. Their theoretical weight is 1.1 g.

b) Batch of Cubes Produced by Adding Active Substances at the Start of Mixing.

In parallel, edible/chewable cubes were manufactured using the same formulation but in accordance with the following method: place the liver powder in a mixer. Previously dissolve the milbemycin in the propylene glycol of the dicapric/dicaprylic acids, vaporise the milbemycin solution and mix until a homogeneous mixture is obtained. Add the praziquantel and mix. Vaporise the previously liquefied triglycerides of capric/caprylic/myristic/stearic acids and mix. Add the PEG 4000, BHA, propyl gallate and mix. Add the gelatine, sugar and mix. Pour the glycerine onto the homogeneous mixture. Mix until a dry, fluid, homogeneous granular material is obtained. Add the precipitated silica and mix. Calibrate the granular material through a screen of mesh size 800 μm. The edible/chewable cubes of parallelepiped shape and size of 12.5×12.5×7 mm are obtained by compression at 40 kN using a press for compressing formulas with high fat content. Their theoretical weight is 1.1 g.

For both batches, all the cubes were weighed separately. No cube differed by more than 2% from the theoretical weight. This would not have been possible using the techniques usually used, namely extrusion which is a continuous production technique, or moulding with a paste.

For both batches, determination of the milbemycin content for the 5 lightest edible/chewable cubes and the 5 heaviest showed that the mixture was perfectly homogeneous since the dosage values all lay within the dose range of theoretical dose permitted for medicinal products. This determination, performed on a semi cube just after the preparation thereof was repeated one year later after storage at 25° C. on the other half of the cube. For the cubes obtained according to the invention, the dosage values for each cube after a storage period of one year did not differ by more than 3% from the values obtained just after compression of the cubes, which was not the case for the cubes in the second batch for which a loss of more than 10% of active substance was recorded.

Having regard to margins of error for dosages, to degradation during the storage period (variations) permitted for medicinal products, the invention evidences perfect stability of the molecule even if it is sensitive or fragile.

EXAMPLE 2—MONADIC APPETENCY TEST WITH THE EDIBLE/CHEWABLE CUBES

An appetency test of the edible/chewable cubes obtained according to the invention in Example 1 was performed on thirty male and female adult dogs of varied races. The dogs weighing 5 kg to 25 kg were given 5 cubes and dogs weighing 25 to 50 kg were given 10 cubes. The cubes were given at the same time.

This was a monadic test conducted in individual boxes for ten minutes per dog. The following were measured:

taking from the hand/from the ground/or not taken consumption: total/partial/not eaten.

For each of these criteria, the number of individual dogs is specified for the entire panel and per size category (small/medium/large). The calculation of acceptability was based on the percentage number of dogs which ate the entire edible/chewable cube.

Taking:

|  | dogs weighing 5 to 25 kg | dogs weighing 25 to 50 kg |
| --- | --- | --- |
| From the hand | 20 | 10 |
| From the ground | 0 | 0 |
| Not taken | 0 | 0 |

Consumption:

|  | dogs weighing 5 to 25 kg | dogs weighing 25 to 50 kg |
| --- | --- | --- |
| Partial | 0 | 0 |
| Full | 20 | 10 |
| Not eaten | 0 | 0 |

There was total acceptability and consumption of the edible/chewable cubes according to the invention (100%).

EXAMPLE 3—PREPARATION OF EDIBLE/CHEWABLE CUBES FOR DOGS

Edible/chewable cubes of 1.1 g containing 68 μg ivermectin, 57 mg pyrantel in pamoate form and 57 mg of praziquantel according to the invention were prepared using the following composition:

| | |
| --- | --- |
| Coated ivermectin | 2.85% |
| Coated pyrantel pamoate | 5.13% |
| Coated praziquantel | 3.21% |
| Liver powder | 44.80% |
| Hydrogenated palm oil | 6.00% |
| Glycerine | 18.00% |
| PEG 4000 | 12.00% |
| Gelatine | 8.00% |
| Tenox 8 | 0.01% |

In a mixer add the liver powder, PEG 4000, hydrogenated palm oil, Tenox 8 and mix. Add the gelatine and mix. Pour the glycerine onto the homogeneous mixture. Mix until a dry, fluid homogeneous granular material is obtained. Add the coated ivermectin, coated praziquantel, coated pyrantel pamoate and mix. Calibrate the granular material through a screen of 800 μm mesh size. Edible/chewable cubes of parallelepiped shape and size 12.5×12.5×7 mm are obtained by compression at 40 kN using a press for compressing formulas with high fat content. Their theoretical weight is 1.1 g.

All the edible/chewable cubes were weighed separately; no cube differed by more than 2% from the theoretical weight. The determination of the ivermectin content for the 5 lightest edible/chewable cubes and the 5 heaviest showed that the mixture was perfectly homogeneous since the dosage values all lay within the dose range of theoretical dose permitted for medicinal products. This determination, performed on a semi-cube just after the preparation thereof was repeated one year later after storage at 25° C. on the other half of the cube. The dosage values for each semi-cube after a storage period of one year did not differ by more than 3% from the values obtained just after compression of the cubes. Having regard to margins of error for dosages and to degradation during the storage period (variations) permitted for medicinal products, the invention evidences perfect stability of a molecule even if it is sensitive or fragile.

EXAMPLE 4—COMPARATIVE HOMOGENEITY TEST BETWEEN THE WEIGHTS OF THE Edible/Chewable Cubes and Chewable Tablets Obtained by Extrusion Twenty edible/chewable cubes obtained according to the invention and conforming to Example 1 were taken consecutively from the production line and weighed.

A batch of chewable tablets was produced by extrusion having the following formula:

| | |
| --- | --- |
| Ivermectin | 0.001236% |
| Pyrantel pamoate | 2.963636% |
| Suet | 2.5% |
| Beef meat | 42.0% |
| Soy flour | 30.932404% |
| Salt | 2.00% |
| Molasses | 8.00% |
| Propylene glycol | 5.0% |
| Glucono delta lactone | 3.30% |
| Potassium sorbate | 0.30% |
| Propyl gallate | 0.0005% |
| BHA | 0.0018% |
| Citric acid | 0.0004% |

Similarly, twenty tablets were taken consecutively from the production line and weighed. The weights recorded for the two samplings of twenty items are given in the following Table:

| Item N° | Chewable cube Weight in grams | Chewable tablet Weight in grams |
| --- | --- | --- |
| 1 | 5.53 | 5.55 |
| 2 | 5.56 | 4.83 |
| 3 | 5.51 | 5.92 |
| 4 | 5.49 | 5.49 |
| 5 | 5.42 | 6.24 |
| 6 | 5.41 | 4.86 |
| 7 | 5.53 | 5.69 |
| 8 | 5.56 | 6.27 |
| 9 | 5.60 | 4.78 |
| 10 | 5.59 | 4.96 |
| 11 | 5.55 | 5.67 |
| 12 | 5.48 | 6.13 |
| 13 | 5.45 | 6.06 |
| 14 | 5.49 | 5.19 |
| 15 | 5.50 | 5.43 |
| 16 | 5.47 | 4.99 |
| 17 | 5.57 | 4.75 |
| 18 | 5.52 | 5.78 |
| 19 | 5.49 | 6.01 |
| 20 | 5.55 | 5.26 |
| Difference | <2% | >14% |

A large difference, higher than 14%, was observed between the extreme weights of the chewable tablets and the mean weight of the 20 chewable tablets obtained by extrusion, as compared with the weight difference, less than 2%, found with the edible/chewable cubes obtained according to the invention.

These weight differences necessarily lead to a variation of at least the same magnitude in the quantities of active molecules contained in the chewable tablets. It cannot be envisaged to use the extrusion or moulding process for producing unit forms of medicinal products unless the chewable tablets are weighed one by one on leaving the conforming machine with the discarding of all those which do not come within the weight range guaranteeing a quantity of active molecules such as laid down by regulations on medications. If, as a first approach in the example given, only those chewable tablets were retained whose weight did not differ by more than 5 percent from the theoretical weight, only 6 of the chewable tablets out of the twenty produced would be retained i.e. 30% of the production, which is not economical and without any guaranteed quantity of the active molecules contained in the chewable tablets having a weight close to or equivalent to the upper and lower weight limits for selection of the chewable tablets. Similarly it cannot be envisaged to extrude or mould the discarded chewable tablets a second time since the available active molecules would inevitably be modified and would lead to modification of the therapeutic activity.

EXAMPLE 5—FORMULATIONS

Other formulations conforming to the invention are described below. Edible/chewable cubes containing 68 µq of ivermectin and 57.5 mg of pyrantel in pamoate form according to the invention were produced with the following composition:

| | |
|---|---|
| Ivermectin | 0.001236% |
| Pyrantel pamoate | 2.963636% |
| Rapeseed oil | 5.00% |
| Suet | 10.00% |
| Beef meat | 40.30% |
| Soy flour | 28.132428% |
| Salt | 2.00% |
| Molasses | 8.00% |
| Glucono delta lactone | 3.30% |
| Potassium sorbate | 0.30% |
| Propyl gallate | 0.0005% |
| BHA | 0.0018% |
| Citric acid | 0.0004% |

All the edible cubes were weighed separately; their theoretical weight was 5.5 g. No cube differed by more than 2 percent from the theoretical weight.

The determination of the ivermectin content for the 5 lightest edible/chewable cubes and the 5 heaviest showed that the mixture was perfectly homogeneous since the dosage values all lay within the dose range of theoretical dose permitted for medicinal products.

Edible/chewable cubes for horses were prepared with the following composition:

| | |
|---|---|
| Fermented soy extract | 83% |
| Hydrogenated palm oil | 10% |
| Granulated sugar | 6% |
| Titanium oxide | 0.9% |
| BHA | 0.1% |

Edible/chewable cubes of parallelepiped shape and size 31×23×10 mm were obtained by compression using a stock cube press. All the edible/chewable cubes were weighed separately. No cube differed by more than 2 percent from the theoretical weight.

An appetency test of these edible/chewable cubes was carried out with several horse and pony owners and in a riding centre. The edible/chewable cube was offered to the horse or pony on the outstretched hand. Acceptability and consumption of the edible cubes were total (100%). The behaviour of the animals towards this cube is to be pointed out. Several riders reported that the horses and ponies were greatly attracted by this edible/chewable cube presented in this shape, size and colour. As soon as the first had been eaten they looked for more, putting their noses to the riders' pockets from which the cubes had been taken.

Edible/chewable cubes, for dogs, of 3 g containing 68 µg ivermectin, 57 mg pyrantel in pamoate form and 57 mg praziquantel according to the invention were produced with the following composition:

| | |
|---|---|
| Coated ivermectin | 1.0% |
| Coated pyrantel pamoate | 6.0% |
| Coated praziquantel | 5.0% |
| Liver powder | 46.00% |
| Hard fat | 8.00% |
| Glycerine | 12.00% |
| PEG 4000 | 12.00% |
| Gelatine | 6.00% |
| Sugar | 3.54% |
| Sorbic acid | 0.40% |
| BHA | 0.04% |
| Propyl gallate | 0.02% |

Edible/chewable cubes of parallelepiped shape and size 17×17×9.6 mm were obtained by compression using a stock cube press. All the edible/chewable cubes were weighed separately, their theoretical weight being 3.0 g. No cube differed by more than 2 percent from the theoretical weight.

The invention claimed is:

1. A process for preparing a tablet, wherein the tablet comprises a solid, palatable chewable composition comprising:
   α. 10 to 30% by weight of at least one fatty substance, in solid, waxy or paste form, selected from among a fat, a wax or liquid oil, thickened liquid oil, or mixture thereof; the liquid oil of the liquid or thickened oil not representing more than 8% by weight of the tablet;
   β. 0.001 to 57% by weight of at least one active substance, wherein the active substance uniformly distributes throughout the solid, palatable chewable composition;
   χ. 40 to 96.999% by weight of at least one palatable material;
   δ. optionally one or more additives selected from among fillers, binders, solvents, absorbent/gelling substances, flavourings, surfactants, taste enhancers, sweeteners, anti-oxidants, chelating agents, preserving agents, colouring agents and pH regulators;
   a) the liquid or thickened oil is selected from among olive oil, groundnut oil, rapeseed oil, sunflower, the triglycerides of capric and caprylic acids, the propylene glycol of dicapric/dicaprylic acids, and mixtures thereof;
   b) the fat is selected from among chicken fat, duck fat, lard, suet, butter, palm fat, palm stearin, margarine, palm oil optionally hydrogenated, cetyl palmitate, hydrogenated coconut oil, the triglycerides of capric, caprylic, myristic and stearic acids, and the mixtures thereof;
   c) the wax selected from among beeswax, carnuba wax, candelilla wax, and the mixtures thereof;
   d) the palatable material is selected from among meat, meat powders, fish powders, cheese powders, milk derivatives, liver powder, the extracts of these animal substances or their derivatives; beer yeast; vegetable fibres; vegetable products and by-products, fenugreek, apple, carrot, fodder beet, sugar beet, thyme, alfalfa, sugar cane, cereals, wheat, rice, corn, soy, flours, sugar (sucrose) in all its forms, granulated, caster, icing, glucose, invert sugar, molasses, honey or its derivatives, and the mixtures thereof, salt; and the mixtures thereof;

e) the solid, palatable chewable composition has a unit weight to within 3% of the theoretical value of a required weight, wherein the required weight is determined by the fatty substance, active substance, palatable material, and additives that are used in the composition;

f) the solid, palatable chewable composition is stable for more than one year when stored at ambient temperature;

and in said process comprises the following successive steps:

i) preparing a homogenous granular material comprising the palatable material(s), the fatty substance, and optionally one or more additives;

ii) adding the active substance(s) to the granular material obtained after step i) at ambient temperature under agitation, without addition of water or application of heat;

iii) calibrating the granular mixture obtained after step ii) to retain the granules having a particle size between 50 and 1000 μm;

iv) compressing the calibrated granules obtained after step iii) using a press for compressing formulas having a high fat content;

v) collecting the solid palatable chewable tablet after step iv).

2. The process according to claim 1, wherein step i) comprises the following successive steps:

i1) mixing the palatable material(s) and optionally one or more additives, the palatable materials and optional additives being in powder form;

i2) adding the fatty substance to the mixture obtained after step i1);

i3) mixing or triturating without the addition of water or application of heat until a homogeneous granular material is obtained.

3. The process according to claim 2, wherein step i1) the palatable materials and optional additives have a particle size of less than 200 μm.

4. The process according to claim 1, wherein at step ii) the active substance is in the form of powders or granules.

5. The process according to claim 4, wherein at step ii) the particle size of the active substance is no larger than that of the granular material at step iii).

6. The process according to claim 1, wherein the palatable tablet is in the form of a compact mass of which at least the top and bottom surfaces are planar.

7. The process according to claim 1, wherein the press for compressing the formulas with high fat content is equipped with a cluster-breaker-size grader.

8. The process according to claim 1, wherein the press for compressing formulas with high fat content is equipped with a chilled compression stage.

9. The process according to claim 1, wherein at step iv) the compression force is between 5 and 80 kN.

10. The process according to claim 1, wherein:

the filler is selected from among maltodextrins; cyclodextrins; lactose; talc; silicates; phosphates; cellulose powder; microcrystalline cellulose; mica; carbonates;

the binder is selected from among polyvinyl alcohol polymers, polyvinylpyrrolidone, the copolymers of vinylpyrrolidone and vinyl acetate, carboxymethylcellulose is salts and derivatives, solid polyethylene glycols, and their derivatives, gelatins, alginic aid and its salts, zein, pectins, gum arabic, acacia gum, gum tragacanth, karaya gum, xanthan gum, carrageenans, pullulan polymers, agar polymers, starches and their derivatives, molasses, carbomers, acrylic acid cross-linked with polyakenyl ethers, polycarbophils, and the mixtures thereof;

the solvent is selected from among ethanol, propylene glycol, cetyl alcohol, benzyl alcohol, liquid polyethylene glycols, and the mixtures thereof;

the absorbent/gelling substance is selected from among stearic acid and its derivatives, glyceryl stearates, aluminum or magnesium stearates, hydrogenated castor oil, bentonite, silica derivatives, colloidal silica, precipitated silica, pyrogenated silica, cellulose and its derivatives, methyl or ethyl cellulose, hydroxypropylcellulose, hydroxypropylmethylcellulose, spray-dried whey, starches, and the mixtures thereof;

the surfactant is selected from among glycol esters, glycerol monostearate, the esters of fatty acids and sorbitan, the esters of polyoxyethylenated fatty acids and sorbitan; polyoxyethylenated vegetable oils, polyoxyethylenated castor oils, polyoxyethylenated hydrogenated vegetable oils, polyoxyehtylenated hydrogenated castor oils; lecithin and its soy or egg derivatives, phosphatidylcholine, hydrogenated phosphatidylcholine, lysophosphatidylcholine, hydrogenated lysophosphatidylcholine, and the mixture thereof;

the sweetner is selected from among aspartame; sodium saccharin; thaumatin; polyols, sorbitol, xylitol, isomalt, maltitol, mannitol and lactitol; and the mixtures thereof;

the antioxidant is selected from among ascorbic acid, its salts and derivatives, sodium or potassium metabisulphate, sodium bisulphate, butylhydroxyanisol, butylhydroxytoluene, gallic acid and its derivatives, propyl gallate, and the mixtures thereof;

the chelating agent is selected from EDTA and its salts, tartaric acid and its salts, and the mixtures thereof;

the taste enhance is sodium glutamate;

the preserving agent is selected from among parabens, benzoic acid and its salts, sorbic acids and its salts, and the mixtures thereof;

the colouring agent is elected from among iron oxides, titanium oxide, curcumin, caramel, carotenes, and the mixtures thereof;

the pH regulator is selected from among citric acid, its salts and derivatives, sodium carbonates, delta glucono lactone, and mixtures thereof.

11. The process according to claim 1, wherein the additive(s) represent 0.01 to 25% by weight of the tablet relative to the total weight of the tablet.

12. The process according to claim 1, wherein the active substance is selected from among anti-infectives, antibiotics and sulfonamides, cardiotonics, internal and external antiparasitics, insecticides, insect growth inhibitors, anti-arthritics, anti-inflammatories whether or not steroidal, anti-histaminics, hormones, prostaglandins, substances for digestive therapy, gastro-intestinal dressings and sedatives, anti-ulcer agents and substitution flora, anti-diarrhoeals, hepato-protectors, antispasmodics, laxatives, intestinal antiseptics, substances for respiratory therapy, respiratory analeptics, anti-tissuives, bronchodilators, bronchial and mucolytic fluidfiers and respiratory antiseptics, substances acting on the nervous system, analgesics, sedatives and tranquilizers, anti-epileptics, anaesthetics, orexigenics, anorexigenics, substances for immunity therapy, interleukins and interferon, substance for anticancer therapy, antimitotics and cytostatics, macro-, micro-nutrients and trace elements, vitamins, plant extracts, extracts from animal organs, and the mixtures thereof.

13. The process according to claim 1, wherein the tablet comprises an active medicinal substance selected from among antibiotics, amoxicillin, clavulanic acid, cephalexin, rifaximin, anti-parasitics, ivermectin, moxidectin, milbemycin, pyrantel and its derivatives, the pamoate, praziquantel, benzimidazoles, their salts or derivatives, insecticides, fampronil, cardiotonics, levosimendan, and anti-arthritics, diacerein.

14. The process according to claim 1, wherein the tablet comprises an active neutraceutical or food supplement substance selected from among plant extracts, animal extracts, substitution flora, macro-, micro-nutrients and trace-elements, and the mixtures thereof.

15. A solid, palatable chewable tablet obtained by the process of claim 1.

16. A method for treating mammals in need thereof, except man, by oral administration of the solid, palatable chewable tablet obtained by the process of claim 1.

17. The process according to claim 1, wherein the active substance is also a palatable material.

18. The process according to claim 1, wherein at step iii) the granular mixture is calibrated to retain granules having a particle size of between 200 and 800 μm.

19. The method of claim 16, wherein the mammal is a domestic animal including a dog, a cat, or a horse.

20. A process for preparing a tablet, wherein the tablet comprises a solid, palatable chewable composition comprising:
  α. 10 to 30% by weight of at least one fatty substance, in solid, waxy or paste form, selected from among a fat, a wax or liquid oil, thickened liquid oil, or mixture thereof; the liquid oil of the liquid or thickened oil not representing more than 8% by weight of the composition;
  β. 5 to 57% by weight of at least one active substance sensitive to heat, wherein the active substance uniformly distributes throughout the solid, palatable chewable composition;
  χ. 30-60% by weight of at least one palatable material;
  δ. optionally one or more additives selected from among fillers, binders, solvents, absorbent/gelling substances, flavourings, surfactants, taste enhancers, sweeteners, anti-oxidants, chelating agents, preserving agents, colouring agents and pH regulators;
  a) the liquid or thickened oil is selected from among olive oil, groundnut oil, rapeseed oil, sunflower, the triglycerides of capric and caprylic acids, the propylene glycol of dicapric/dicaprylic acids, and mixtures thereof;
  b) the fat is selected from among chicken fat, duck fat, lard, suet, butter, palm fat, palm stearin, margarine, palm oil optionally hydrogenated, cetyl palmitate, hydrogenated coconut oil, the triglycerides of capric, caprylic, myristic and stearic acids, and the mixtures thereof;
  c) the wax selected from among beeswax, carnuba wax, candelilla wax, and the mixtures thereof;
  d) the palatable material is selected from among meat, meat powders, fish powders, cheese powders, milk derivatives, liver powder, the extracts of these animal substances or their derivatives; beer yeast; vegetable fibres; vegetable products and by-products, fenugreek, apple, carrot, fodder beet, sugar beet, thyme, alfalfa, sugar cane, cereals, wheat, rice, corn, soy, flours, sugar (sucrose) in all its forms, granulated, caster, icing, glucose, invert sugar, molasses, honey or its derivatives, and the mixtures thereof, salt; and the mixtures thereof;
  e) the solid, palatable chew able composition has a unit weight to within 3% of the theoretical value of a required weight, wherein the required weight is determined by the fatty substance, active substance, palatable material, and additives that are used in the composition;
  f) the solid, palatable chewable composition is stable for more than one year when stored at ambient temperature;
  and in said process comprises the following successive steps:
  i) preparing a homogenous granular material comprising the palatable material(s), the fatty substance, and optionally one or more additives;
  ii) adding the active substance(s) to the granular material obtained after step i) at ambient temperature under agitation, without addition of water or application of heat;
  iii) calibrating the granular mixture obtained after step ii) to retain the granules having a particle size between 50 and 1000 μm;
  iv) compressing the calibrated granules obtained after step iii) using a press for compressing formulas having a high fat content;
  v) collecting the solid, palatable chewable tablet after step iv).

21. The process according to claim 20, wherein step i) comprises the following successive steps:
  i1) mixing the palatable material(s) and optionally one or more additives, the palatable materials and optional additives being in powder form;
  i2) adding the fatty substance to the mixture obtained after step i1); and
  i3) mixing or triturating without the addition of water or application of heat until a homogeneous granular material is obtained.

22. The process according to claim 20, wherein the active substance is selected from among anti-infectives, antibiotics and sulfonamides, cardiotonics, internal and external anti-parasitics, insecticides, insect growth inhibitors, anti-arthritics, anti-inflammatories whether or not steroidal, anti-histaminics, hormones, prostaglandins, substances for digestive therapy, gastro-intestinal dressings and sedatives, anti-ulcer agents and substitution flora, anti-diarrhoeals, hepato-protectors, antispasmodics, laxatives, intestinal antiseptics, substances for respiratory therapy, respiratory analeptics, anti-tissuives, bronchodilators, bronchial and mucolytic fluidfiers and respiratory antiseptics, substances acting on the nervous system, analgesics, sedatives and tranquilizers, anti-epileptics, anaesthetics, orexigenics, anorexigenics, substances for immunity therapy, interleukins and interferon, substance for anticancer therapy, antimitotics and cytostatics, macro-, micro-nutrients and trace elements, vitamins, plant extracts, extracts from animal organs, and the mixtures thereof; and wherein the tablet comprises an active medicinal substance selected from among antibiotics, amoxicillin, clavulanic acid, cephalexin, rifaximin, anti-parasitics, ivermectin, moxidectin, milbemycin, pyrantel and its derivatives, the pamoate, praziquantel, benzimidazoles, their salts or derivatives, insecticides, fampronil, cardiotonics, levosimendan, and anti-arthritics, diacerein.

* * * * *